United States Patent
Rennert et al.

(10) Patent No.: US 6,671,542 B2
(45) Date of Patent: *Dec. 30, 2003

(54) NON-INVASIVE METHOD OF DETERMINING SKIN THICKNESS AND CHARACTERIZING LAYERS OF SKIN TISSUE IN VIVO

(75) Inventors: Jessica Rennert, Scottsdale, AZ (US); Glenn Aaron Kees, Tempe, AZ (US); Timothy L. Ruchti, Gilbert, AZ (US)

(73) Assignee: Saensys Medical, Inc., Chandler, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/237,457

(22) Filed: Sep. 5, 2002

(65) Prior Publication Data

US 2003/0009089 A1 Jan. 9, 2003

Related U.S. Application Data

(63) Continuation of application No. 09/514,039, filed on Feb. 25, 2000, now Pat. No. 6,456,870.

(51) Int. Cl.[7] .................................................. A61B 5/00
(52) U.S. Cl. ........................................ 600/475; 600/310
(58) Field of Search ................................. 600/310, 473, 600/475; 356/402; 250/340, 341.1, 339.01

(56) References Cited

U.S. PATENT DOCUMENTS 5,361,758 A * 11/1994 Hall et al. ................... 600/322
6,157,041 A * 12/2000 Thomas et al. ......... 250/339.09
6,456,870 B1 * 9/2002 Rennert et al. ............. 600/310

FOREIGN PATENT DOCUMENTS

WO WO 97/32521 * 9/1997

* cited by examiner

Primary Examiner—Eric F. Winakur
(74) Attorney, Agent, or Firm—Glenn Patent Group; Michael A. Glenn; Christopher Peil

(57) ABSTRACT

A novel approach to measuring the overall and layer-by-layer thickness of in vivo skin tissue based on near infrared absorbance spectra is described. The different biological and chemical compounds present in the various layers of a tissue sample have differing absorbance spectra and scattering properties that enable them to be discerned and quantified, thus allowing an estimate of the thickness of the tissue being sampled. The method of the invention also yields the chemical composition of the absorbing and/or scattering species of each layer. Additionally, a method of path length normalization for the purpose of noninvasive analyte prediction on the basis of skin thickness and layer constituents is provided.

25 Claims, 3 Drawing Sheets

NON-INVASIVE METHOD OF DETERMINING SKIN THICKNESS AND CHARACTERIZING LAYERS OF SKIN TISSUE IN VIVO

This application is a Continuation of U.S. patent application Ser. No. 09/514,039, filed Feb. 25, 2000, now U.S. Pat. No. 6,456,870.

BACKGROUND OF THE INVENTION

1. Technical Field

The invention relates to the measurement of tissue properties. More particularly the invention relates to the measurement of skin thickness based on near-infrared absorbance spectra.

2. Description of the Prior Art

Near infrared (NIR) tissue spectroscopy is a promising noninvasive technology that bases measurements on the irradiation of a tissue site with NIR energy in the 700–2500 nm wavelength range. The energy is focused onto an area of the skin and propagates according to the scattering and absorbance properties of the skin tissue. Thus, energy that is reflected by the skin or that is transmitted through the skin is detected provides information about the tissue volume encountered. Specifically, the attenuation of the light energy at each wavelength is a function of the structural properties and chemical composition of the tissue. Tissue layers, each containing a unique heterogeneous particulate distribution, affect light absorbance through scattering. Chemical components such as water, protein, fat and blood analytes absorb light proportionally to their concentration through unique absorbance profiles or signatures. The measurement of tissue properties, characteristics or composition is based on the technique of detecting the magnitude of light attenuation resulting from its respective scattering and/or absorbance properties.

Blood Analyte Prediction

While noninvasive prediction of blood analytes, such as blood glucose concentration, has been pursued through NIR spectroscopy, the reported success and product viability has been limited by the lack of a system for compensating for variations between individuals that produce dramatic changes in the optical properties of the tissue sample. For example, see O. Khalil *Spectroscopic and clinical aspects of non-invasive glucose measurement.* Clin Chem vol. 45, pp. 165–77 (1999); or J. Roe, B. Smoller. *Bloodless Glucose Measurements,* Critical Reviews in Therapeutic Drug Carrier Systems, vol. 15, no. 3, pp. 199–241, (1998). These variations are related to structural differences in the irradiated tissue sample between individuals and include, for example, the thickness of the dermis, distribution and density of skin collagen and percent body fat. While the absorbance features caused by structural variation are repeatable by subject, over a population of subjects they produce confounding nonlinear spectral variation. See C. Tan, B. Statham, R. Marks and P. Payne. *Skin thickness measurement by pulsed ultrasound: its reproducibility, validation and variability,* British Journal of Dermatology, vol. 106, pp. 657–667, (1982). Also see S. Shuster, M. Black and E. McVitie, *The influence of age and sex on skin thickness, skin collagen and density,* British Journal of Dermatology, vol. 93, (1975). See also J. Durnin, and M. Rahaman, *The assessment of the amount of fat in the human body from measurements of skin fold thickness,* British Journal of Nutrition, vol. 21, (1967).

Additionally, variations in the subject's physiological state affect the optical properties of tissue layers and compartments over a relatively short period of time. Such variations, for example, may be related to hydration levels, changes in the volume fraction of blood in the tissue, hormonal stimulation, temperature fluctuations and blood hemoglobin levels. The differences in skin thickness and the composition of the different layers produce a confounding effect in the noninvasive prediction of blood analytes.

While these structural and state variations are the largest sources of variation in the measured near-infrared absorbance spectra, they are not indicative of blood analyte concentrations. Instead, they cause significant nonlinear spectral variation that limits the noninvasive measurement of blood analytes through optically based methods. For example, several reported methods of noninvasive glucose measurement develop calibration models that are specific to an individual over a short period of time. See K. Hazen, *Glucose determination in biological matrices using near-infrared spectroscopy,* Doctoral Dissertation, University of Iowa, (August 1995). Also see M. Robinson, R. Eaton, D. Haaland, G. Koepp, E. Thomas, B. Stallard and P. Robinson, *Noninvasive glucose monitoring in diabetic patients: a preliminary evaluation,* Clin. Chem, vol. 38/9, pp. 1618–1622, (1992). Also see S. Malin, T. Ruchti, T. Blank, S. Thennadil and S. Monfre, *Noninvasive prediction of glucose by near-infrared diffuse reflectance spectroscopy,* Clin. Chem, vol. 45:9, pp. 1651–1658, (1999).

A related application, S. Malin, T. Ruchti, *An Intelligent System For Noninvasive Blood Analyte Prediction,* U.S. patent application Ser. No 09/359,191; filed Jul. 22, 1999, disclosed an apparatus and procedure for substantially reducing this problem by classifying subjects according to spectral features that are related to the tissue characteristics prior to blood analyte prediction. The extracted features are representative of the actual tissue volume irradiated. The groups or classes are defined on the basis of tissue similarity such that the spectral variation within a class is small compared to the variation between classes. These internally consistent classes are more suitable for multivariate analysis of blood analytes since the largest source of spectral interference is substantially reduced. In this manner, by grouping individuals according to the similarity of spectral characteristics that represents the tissue state and structure, the confounding nonlinear variation described above is reduced and prediction of blood analytes is made more accurate.

The general method of classification relies on the determination of spectral features most indicative of the sampled tissue volume. The magnitude of such features represents an underlying variable, such as the thickness of tissue or level of hydration. It would therefore be highly advantageous to have a non-invasive method of determining skin thickness and characterizing the chemical and structural properties of the various layers.

Skin Thickness Determination

Skin thickness determinations are valuable for several purposes. The thickness of skin tissue and the individual layers provide valuable diagnostic information in a number of circumstances. For example, skin thickness is an important indicator of changes in the skin due to chronological ageing and photo ageing. Skin thickness measurements also provide important information related to a variety of endocrine disorders. Furthermore, a relationship between skin thickness and bone density has been observed. Therefore, skin thickness measurements have potential application in the diagnosis and monitoring of bone loss disorders.

As discussed above, the skin thickness measurement provides information about one of the primary sources of tissue variability and is therefore effective for establishing the general category of the tissue structure. The various categories are suitable for further spectral analysis and calibrations such as blood analyte measurement. Finally, the thickness can be used in conjunction with a diffuse reflectance spectrum for the purpose of path length normalization in spectroscopic examination of the skin.

The most common method of determining the thickness of the skin and its constituent layers is through histological examination of a biopsy specimen. Biopsy has the obvious disadvantage of being an invasive procedure. The subjects must endure an appreciable level of inconvenience and discomfort, and they are exposed to the risks associated with any surgical procedure. It is also a time-consuming, multi-step procedure, requiring skilled medical personnel and multiple pieces of equipment. The ensuing histological examination requires specialized equipment and personnel trained in special laboratory techniques such as tissue sectioning. A simple, non-invasive method of determining skin thickness in vivo would be highly useful.

In fact, a non-invasive method of skin thickness determination using ultrasonography is known [see Tan, et al.]. A beam of ultrasound is directed toward a target site. The reflected ultrasound is detected and an image, or sonogram, of the site is generated. Subsequent visual inspection of the resulting image allows an estimation of overall skin thickness. While this method circumvents the obvious disadvantages of biopsy and histological examination, its utility is limited to providing a macroscopic image of the targeted tissue, reflecting the state of the tissue at the time of examination. Ultrasonography cannot provide detailed information concerning the individual tissue layers. It would be desirable to have a quantitative method of skin thickness determination that also allowed the structural and chemical characterization of the individual layers that the skin comprises, and that provided data for further analysis and classification, such as blood analyte prediction.

SUMMARY OF THE INVENTION

Disclosed is a novel approach to measuring the overall and layer-by-layer thickness of in vivo skin tissue based on near infrared absorbance spectra. The disclosed methods also yield the chemical composition of the absorbing and/or scattering species of each layer. Finally, a method of path length normalization for the purpose of noninvasive analyte prediction on the basis of skin thickness and layer constituents is disclosed.

All procedures are based on the measurement of the absorbance of near-infrared light at a target tissue site. Near infrared measurements are made either in transmission or diffuse reflectance using commonly available NIR spectrometers, or by means of an LED array, to produce a spectrum of absorbance values. The method of skin thickness measurement relies on the fact that different biological and chemical compounds have differing absorbance spectra and scattering characteristics that can be discerned and quantified accordingly. These and other features, aspects and advantages of the invention will be better understood with reference to the following description, drawings and appended claims.

DETAILED DESCRIPTION

The invention provides two general methods of skin thickness prediction on the basis of near-IR (NIR) spectral measurements. The first method also yields information relating to the structure and composition of the absorbing and scattering species in each layer. Further, knowledge of the thickness and optical properties of the individual tissue layers can be applied in a method of pathlength normalization to minimize the interference due to the variation of the individual layers.

Method 1—Determination of Skin Thickness on the Basis of Marker Constituents

The primary method takes advantage of the presence of key indicators. Key indicators are the chemical or structural components that are primary absorbers and/or scatterers in each particular tissue layer, and that are not present in significant amounts (spectrally) in other layers. This allows for the exploitation of distinct spectral characteristics and features that are specific to certain tissue regions, or layers, based solely on such spectral measurements. The spectral manifestation of these key indicators makes it possible to quantify the primary constituents and to determine the thickness of the individual tissue layers.

The key indicators are determined from a priori knowledge of the composition and structure of skin tissue layers. Examples of key indicators are provided in the table below:

| Key Indicator | Tissue Region of Significance |
| --- | --- |
| Triglycerides | Subcutaneous Tissue |
| Collagen Bundles | Dermis |
| Water | Dermis |
| Blood | Dermis |
| Keratinocytes | Epidermis |
| Lipids (Fatty Acids) | Epidermis |
| Lipids, Specialized (Sterols, Sphingolipids) | Epidermis |
| Pigments | Epidermis |
| Corneocytes, Keratinized Cells | Stratum Corneum |
| Sebum | Stratum Corneum |

For example, because water is present in the dermis in greater concentration than in the epidermis or subcutaneous tissue, water is specified as a key indicator for the dermis. Similarly, because high concentrations of triglycerides are found primarily in adipose tissue with relatively little found in the epidermis or dermis, trigylcerides are specified as a key indicator for adipose tissue, also known as subcutaneous tissue. Collagen bundles can be used as an additional key indicator for the dermis. The epidermis can be discriminated by the scattering and/or absorbance of keratinocytes, while the stratum corneum is distinguished by the scattering and absorbance of corneocytes, keratinized cells, and specialized lipids.

Figure 1:
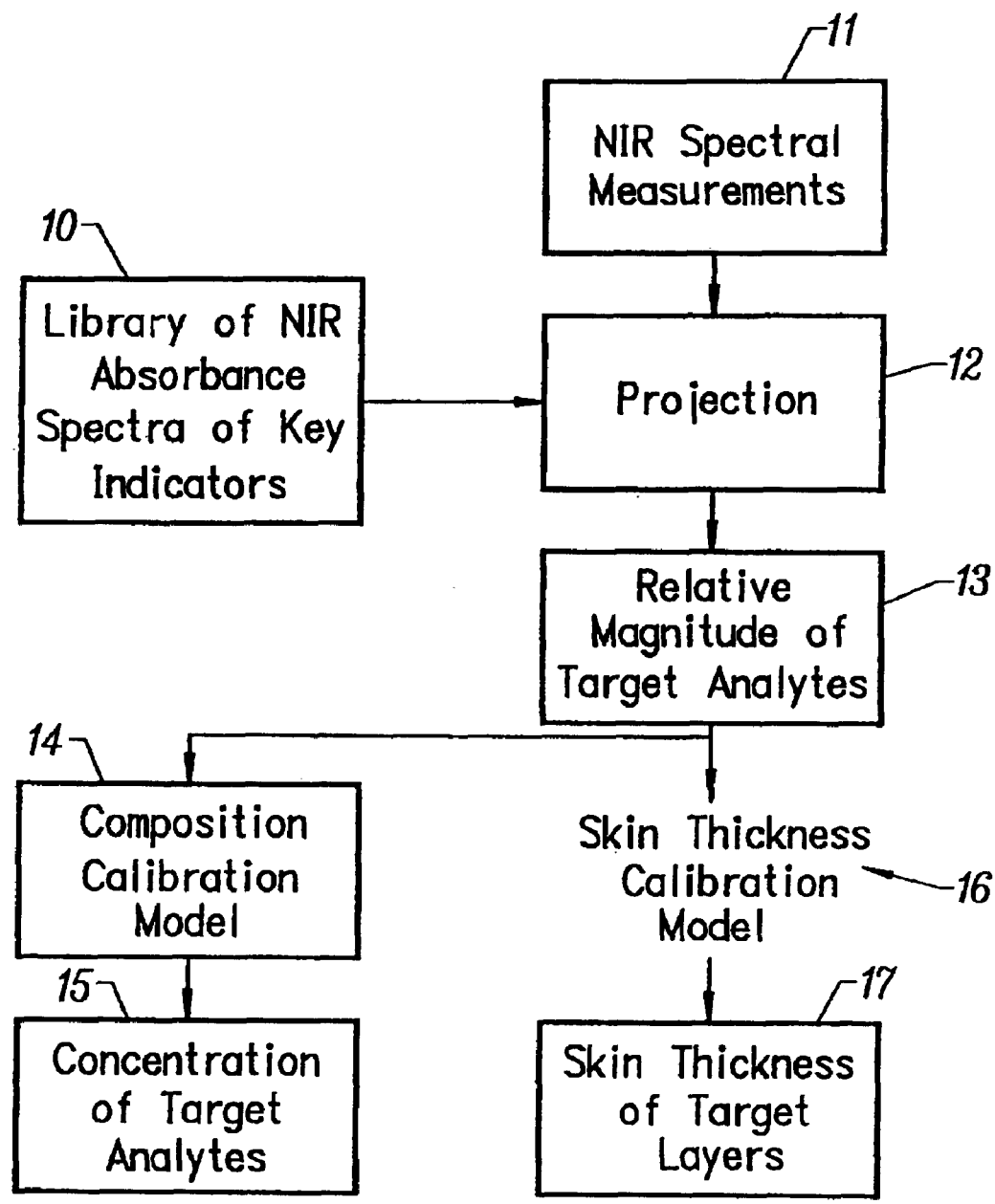
FIG. 1 is a block diagram of a general procedure for determining the magnitude of target analytes and the skin thickness of target layers according to the invention.

The procedure for measuring the magnitude of the key indicators and skin thickness is shown in FIG. 1. First, a library of normalized NIR absorbance spectra 10 of the key indicators is provided. The spectra 10 of the key indicators are stored in the memory of a computer associated with a spectrometer device. A suitable system for executing the procedures and methods disclosed herein is described in a related application to the current application, T. Ruchti, S. Malin *An Intelligent System for Noninvasive Blood Analyte*

*Prediction,* U.S. patent application Ser. No. 09/359,191, filed Jul. 22, 1999. A NIR absorbance measurement 11 of the targeted tissue site is made in the wavelength region(s) in which both the key indicators specific to the target layer absorb or scatter and in which light penetration to the target tissue layer is optimal. The normalized pure component spectra of the key indicators are projected 12 onto the measured absorbance spectrum. Alternately, the spectra of the key indicators are used as a basis set and the method of partial least squares is used to determine the optimal magnitude of each to represent the measured absorbance spectrum.

The calculated magnitude 13 of each normalized key indicator provides a relative concentration of its respective constituent in the tissue. A composition calibration model 14 is applied to the calculated magnitudes to determine the actual concentration 15 of the constituent. In the related application cited above U.S. patent application Ser. No. 09/359,191, a detailed description of a procedure for calculating such a calibration model is given.

Alternatively, the relative concentrations of the key indicators are processed by an alternate calibration model 16 for estimating skin thickness to determine the thickness of the target layer 17. It will be apparent to one skilled in the art that since key indicators are specific to a given layer, their relative absorbances are directly related to the thickness of the targeted layer(s). One skilled in the art will further appreciate that an overall thickness estimate may be arrived at by a simple summing of the thickness estimates of the individual layers.

The skin thickness calibration model 16 is calculated from a calibration set (not shown) of exemplary measurements that provides both the relative concentrations of the key indicators, calculated from absorbance spectra, and the thickness of each tissue layer. The calibration model is determined through multiple linear regression, partial least squares regression, artificial neural networks or other techniques such that the thickness of each layer is predicted through a mathematical mapping of the relative magnitude of the marker constituents. The related application Ser. No. 09/359,191, previously referred to, provides a detailed description of a procedure for calculating the skin thickness calibration model 16 heretofore described.

Two alternative experimental methods for realizing the calibration set are provided below. In the first method, spectral measurements of a target area of human skin are obtained using a NIR reflectance instrument. Biopsies of the scanned region are then obtained and examined histologically. The thickness and chemical composition of the key indicators specific to each tissue layer were included in the calibration set. Using multivariate regression analysis techniques, a calibration model can then be developed to relate the spectral skin measurements, known as predictor variables, to the known skin layer thickness and chemical compositions, known as response variables. This technique uses a priori information regarding the general physiology of skin and exploits the inherent difference between skin layers and their compositions to develop a model that predicts skin layer thickness and composition noninvasively.

The second approach is to develop a tissue model that adequately represents the fundamental absorbing and scattering characteristics of an in vivo tissue system. Although, living tissue is a highly complex system, the transform from an in vivo system to a tissue model is made possible by an a priori knowledge of the primary absorbing and scattering species present in the living tissue system. Becasue the model also includes a known thickness for each tissue layer, and since the concentrations of absorbing and scattering components are known, a Monte Carlo simulation may be used to simulate the photon propagation of light through the tissue model. The result of the Monte Carlo simulation is a diffuse reflectance measurement that is comparable to an actual reflectance measurement obtained experimentally. The tissue model must be validated in order to confirm that the model mirrors the complexity of the living tissue with sufficient accuracy to produce analogous results in application.

Experimental Results

Figure 2:
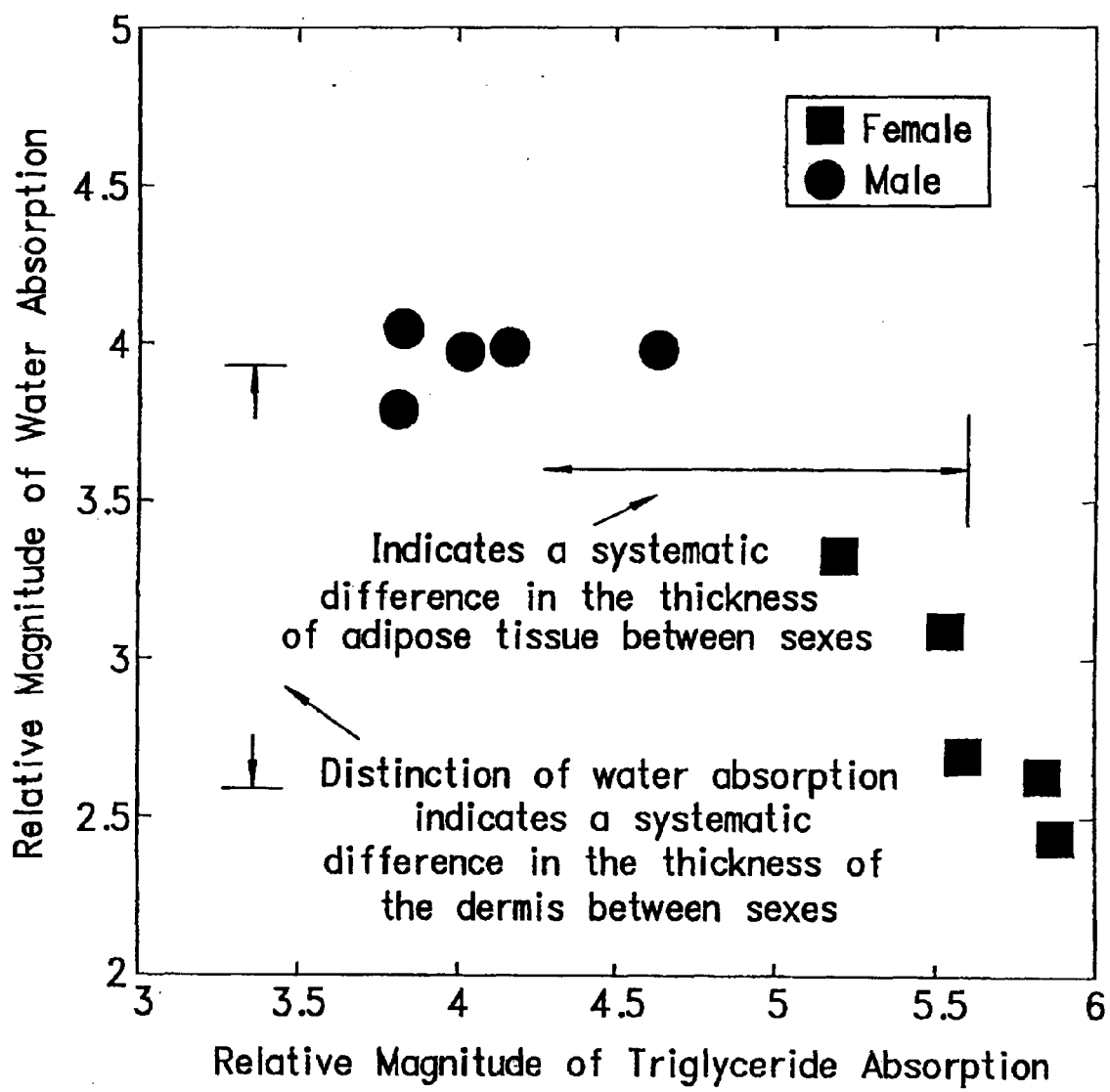
FIG. 2 shows relative magnitudes of water and trigylcerides for 10 subjects, plotted by sex according to the invention.

A study was performed using ten subjects, five males and five females. NIR absorbance spectra were collected using a custom spectrometer in diffuse reflectance mode. The pure component absorbance spectrum of water and fat were projected onto the measured spectrum in the 1100–1400 nm range and the resulting magnitudes are plotted, by sex, in FIG. 2. The figure shows a systematic difference in the relative magnitudes of the key indicators by sex. The subjects assorted into two distinct groups, with the males tending to exhibit high magnitudes of water absorbance, indicating a relatively thicker dermis, and low magnitudes of triglyceride absorbance, indicating a relatively thinner subcutaneous or adipose layer. Conversely, the females tended to exhibit low magnitudes for water absorbance and high magnitudes for triglyceride absorbance, suggesting a relatively thinner dermis and a relatively thicker subcutaneous or adipose layer. Such a systematic difference is consistent with that reported in the literature, i.e. a thicker layer of adipose tissue in females than in males and a thinner dermis in females than males [see Tan, et al., op.cit.]. Thus, the gross measurement of relative skin thickness through an NIR diffuse reflectance measurement is amply demonstrated. Quantification of the measurement is accomplished through calibrations based on prior in vivo measurements or Monte Carlo simulations as described above.

Method 2—Skin Thickness on the Basis of a General Calibration Model

The second method employs a general calibration model to predict the total skin thickness or the thickness of target layers on the basis of the measured absorbance spectrum. In overview, the method includes the following steps:

providing a calibration set of exemplary measurements;

measuring the NIR spectrum of a target layer at a tissue site;

processing the NIR spectral measurement through a general calibration model; and arriving at an thickness estimate of the targeted tissue layer.

As previously described, an estimate of total thickness is derived by summing the thickness estimates for the individual tissue layers. The general calibration model is based on a calibration set that includes spectral measurements, as previously described, made at a target tissue measurement site on a diverse group of individuals, and thickness measurements of the individual layers based on histological analysis of biopsy results or another commonly accepted method of skin thickness determination, pulsed ultrasound for example. The calibration model is developed using known methods, including principal component regression partial least squares regression and artificial neural network (see H. Martens, T. Naes. *Multivariate Calibration,* New York: John Wiley and Sons, (1989); P. Geladi, B. Kowalski, *Partial least-squares regression: a tutorial,* Analytica Chimica Acta, vol. 185, pp. 1–17, (1986)). New absorbance spectra are then processed through the calibration model to arrive at an estimate of skin thickness for the corresponding tissue sample.

Experimental Results

Figure 3:
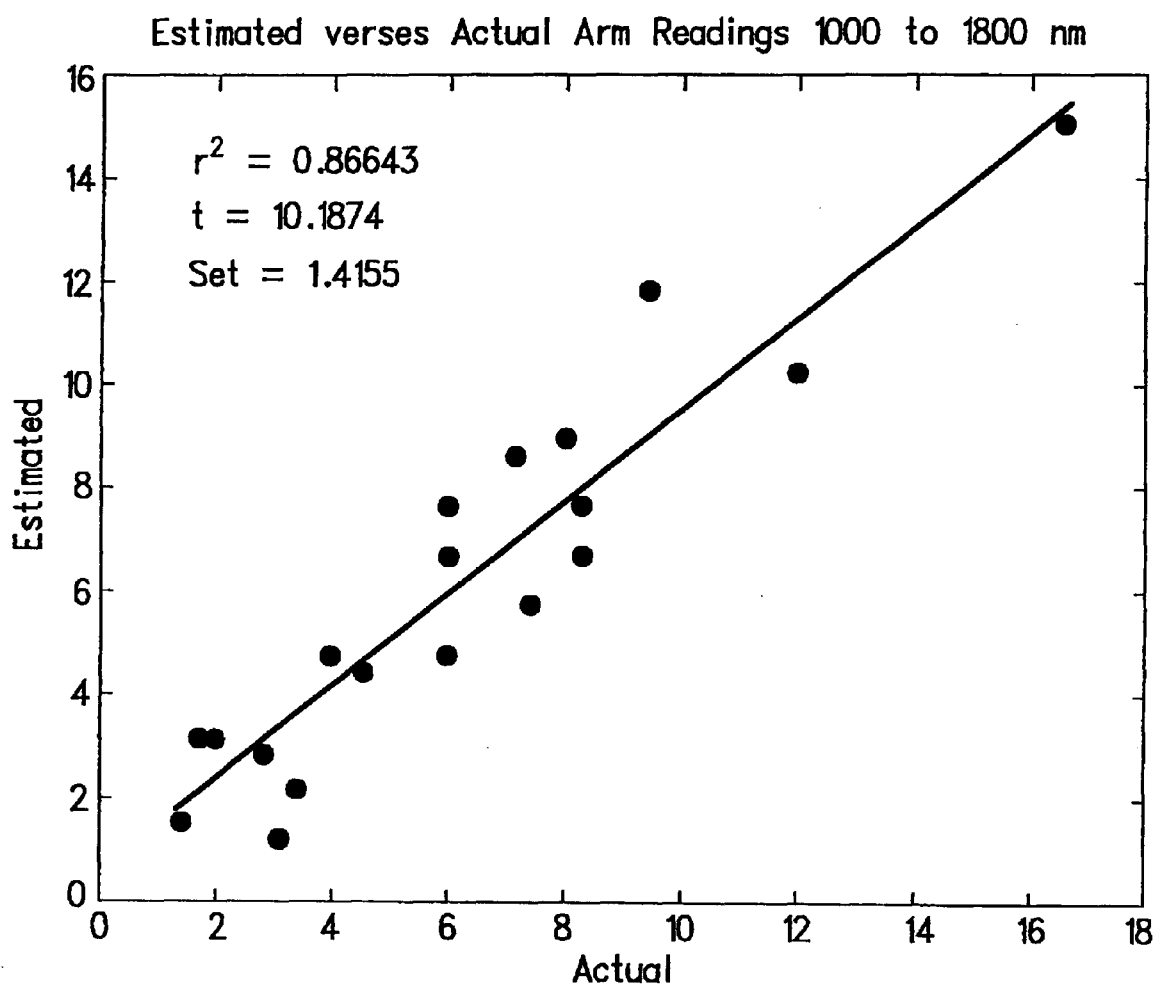
FIG. 3 shows a plot of estimated skin fold thickness versus actual skin fold thickness for nineteen subjects according to the invention.

A study was performed involving nineteen volunteers of diverse age (21–55 years) and sex (sixteen males and three females). Skin fold thickness of each participant was measured on the forearm with research grade calipers of the type known as HARPENDEN, manufactured by British Indicators, LTD. NIR scans of each subject were taken on the forearm and a calibration model for predicting the skin fold thickness was developed using partial least squares regression. The model was evaluated through cross-validation and the results are shown in FIG. 3. Estimated versus actual skinfold thickness determination were plotted for each subject. The standard error of prediction was 1.42, yielding a prediction accuracy of 70 percent. The results clearly demonstrate the feasibility of determining the thickness of a target layer from a general calibration model.

Pathlength Normalization

The differences in skin thickness and the composition of the different layers produce a confounding effect in the noninvasive prediction of blood analytes. In one individual, at a particular time, an absorbance spectrum is representative of a distinct tissue volume that is sampled by the penetration of the light. When the target analyte for prediction is present in a particular layer it absorbs the light in a manner that is determined by its concentration and the pathlength of light within the particular layer. However, this pathlength is a function of the optical properties of the layer and the optical properties of the surrounding layers. Therefore, knowledge of the thickness of individual skin layers and their optical properties can be used to reduce the interference resulting from this nonlinear variation.

The skin thickness can be used in a classification system that develops calibrations specific to groups or classes of individuals based on tissue structure and state, fully described by Malin, et al. in the previously cited related application Ser. No. 09/359,191. However, in an alternative method for reducing interference due to non-linear variation, skin thickness and composition can be used with a nonlinear function to normalize the measured spectrum. The function can be determined from the light distributions in Monte Carlo simulations involving skin models of diverse composition and thickness.

Although the invention has been described herein with reference to certain preferred embodiments, one skilled in the art will readily appreciate that other applications may be substituted for those set forth herein without departing from the spirit and scope of the present invention. Accordingly, the invention should only be limited by the claims included below.

What is claimed is:

1. A non-invasive method of estimating thickness of in vivo skin tissue and characterizing constituents of tissue layers, comprising the steps of:
   measuring a NIR absorbance spectrum of a target layer at a tissue sample site;
   processing said measured NIR absorbance spectrum to enhance a signal of a plurality of key indicators;
   calculating a magnitude or a relative magnitude of at least one of said key indicators in said measured spectrum; and
   applying at least one calibration model to said calculated magnitude or relative magnitude to characterize said tissue layers.

2. The method of claim 1, wherein said step of processing said measured NIR absorbance spectrum comprises:
   projecting normalized spectra of said key indicators on said measured spectrum.

3. The method of claim 1, wherein said key indicators comprise chemical and structural components that are primary absorbers and scatterers within a particular tissue layer, and wherein said magnitude of said key indicators is greater in said particular layer of said tissue sample than in any other layer of said tissue sample, such that said magnitude of said key indicators is specific to said particular tissue layer, and whereby said particular tissue layer can be characterized according to said magnitudes of said key indicators.

4. The method of claim 3, wherein tissue layers that can be characterized by calculating said magnitudes of said key indicators include any of:
   subcutaneous tissue;
   dermis;
   epidermis; and
   stratum corneum.

5. The method of claim 3, wherein said key indicators are determined from a priori knowledge of the composition and structure of said tissue layers, and wherein structural and chemical components that can serve as said key indicators include any of:
   triglycerides;
   collagen bundles;
   water;
   blood;
   keratinocytes;
   fatty acids;
   sterols;
   sphingolipids;
   pigments;
   corneocytes;
   keratinized cells; and
   sebum.

6. The method of claim 3, wherein said measuring step comprises the steps of:
   selecting a target tissue layer;
   selecting at least one target key indicator specific to said target tissue layer; and
   limiting said spectrum to a wavelength region wherein said at least one target key indicator absorbs and scatters, and wherein optimal penetration of transmitted energy to said target layer is possible.

7. The method of claim 3, wherein said plurality of key indicators comprises a basis set.

8. The method of claim 3, wherein said calculation step comprises the step of:
   applying a partial least squares regression to calculate said magnitudes.

9. The method of claim 3, wherein said calculated magnitudes of said key indicators provide relative concentrations of said structural and chemical components.

10. The method of claim 3, further comprising the step of:
    providing a calibration set of exemplary measurements.

11. The method of claim 10, wherein said step of applying at least one calibration model comprises the step of:
    applying at least one calibration model to said relative concentrations to determine an actual concentration in said target layer, wherein said calibration model is calculated from said calibration set.

12. The method of claim 10, wherein said step of applying at least one calibration model comprises the step of:
    applying said calibration model to said relative concentrations to determine absolute or relative thickness of said target layer, wherein thickness is any of physical and optical thickness; and wherein said calibration model is calculated from said calibration set.

13. The method of claim 12, further comprising the step of:

summing thickness estimates.

14. The method of claim 13, wherein said calibration set comprises spectral measurements of a target tissue site and tissue layer thickness determinations from an exemplary population of subjects.

15. The method of claim 14, wherein multivariate regression analysis relates said exemplary spectral measurements to said exemplary tissue layer thickness determinations.

16. The method of claim 10, wherein said exemplary measurements comprise calculated relative concentrations of said chemical and structural components and tissue layer thickness determinations.

17. The method of claim 16, wherein said calibration model is calculated using any of multiple linear regression, partial least squares regression, and artificial neural networks.

18. The method of claim 10, wherein said calibration set comprises NIR spectral measurements of an exemplary sample of skin tissue, tissue layer thickness measurements determined from biopsies of said exemplary sample, and determinations of chemical composition of said layers of said biopsy samples.

19. The method of claim 18, wherein multivariate regression analysis relates said NIR spectral measurements of said exemplary tissue sample to said layer thickness and chemical composition determinations from said biopsy samples.

20. The method of claim 10, wherein said calibration set comprises a tissue model that represents the fundamental absorbing and scattering characteristics of an in vivo tissue system.

21. The method of claim 20, wherein said tissue model employs a simulation method whereby photon propagation of light through said tissue model is simulated, and wherein said photon propagation simulation yields a simulated diffuse reflectance spectrum comparable to an actual reflectance spectrum.

22. The method of claim 21, wherein said simulation method is a Monte Carlo simulation.

23. A non-invasive method of estimating thickness of in vivo skin tissue comprising the steps of:

measuring an NIR absorbance spectrum of a target layer at a tissue sample site;

applying at least one calibration model to said absorbance spectrum; and determining a thickness estimate of said target layer of said tissue sample; and summing thickness estimates of individual target layers so that a total thickness of said tissue sample is calculated.

24. The method of claim 23, further comprising the step of:

providing a calibration set of exemplary measurements.

25. The method of claim 24, wherein said calibration model is calculated from said calibration set using any of multiple linear regression, partial least squares regression, and artificial neural networks.

* * * * *